United States Patent [19]

Maurer et al.

[11] 4,127,652
[45] Nov. 28, 1978

[54] COMBATING PESTS WITH (-O-ALKYL-O-[PYRIMIDIN(5)YL]-(THIONO) THIOL) PHOSPHORIC(PHOSPHONIC) ACID ESTERS AND ESTER-AMIDES

[75] Inventors: Fritz Maurer; Rolf Schröder, both of Wuppertal; Ingeborg Hammann, Cologne; Wolfgang Behrenz, Overath; Bernhard Homeyer, Leverkusen, all of Fed. Rep. of Germany

[73] Assignee: Bayer Aktiengesellschaft, Leverkusen, Fed. Rep. of Germany

[21] Appl. No.: 834,940

[22] Filed: Sep. 20, 1977

[30] Foreign Application Priority Data

Sep. 25, 1976 [DE] Fed. Rep. of Germany ....... 2643262
Feb. 14, 1977 [DE] Fed. Rep. of Germany ....... 2706127

[51] Int. Cl.² .......................... A01N 9/36; C07F 9/65
[52] U.S. Cl. ..................................... 424/200; 544/243
[58] Field of Search ................. 260/251 P, 256.4 E, 260/256.5 R; 424/200

[56] References Cited
U.S. PATENT DOCUMENTS
2,754,243 7/1956 Gysin et al. .......................... 424/200

FOREIGN PATENT DOCUMENTS
1,140,580 12/1962 Fed. Rep. of Germany ........... 424/200
2,360,877 6/1975 Fed. Rep. of Germany ....... 260/251 P Primary Examiner—Donald G. Daus
Assistant Examiner—Diana G. Rivers
Attorney, Agent, or Firm—Sprung, Felfe, Horn, Lynch & Kramer

[57] ABSTRACT

O-Alkyl-O-[pyrimidin(5)yl]-(thiono)(thiol)-phosphoric (phosphonic) acid ester or ester-amide of the formula

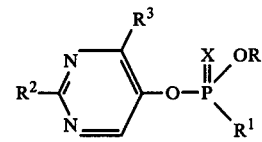

in which
  R is alkyl,
  $R^1$ is alkyl, alkoxy, alkylthio, monoalkylamino or phenyl,
  $R^2$ is hydrogen, alkyl or phenyl,
  $R^3$ is hydrogen or alkyl, and
  X is oxygen or sulphur, which possess arthropodicidal and nematicidal properties.

10 Claims, No Drawings

COMBATING PESTS WITH O-ALKYL-O-[PYRIMIDIN(5)YL]-(THIONO)(THIOL) PHOSPHORIC(PHOSPHONIC) ACID ESTERS AND ESTER-AMIDES

The present invention relates to and has for its objects the provision of particular new O-alkyl-O-[pyrimidin(-5)yl]-(thiono) (thiol) phosphoric (phosphonic) acid esters and ester-amides which possess arthropodicidal and nematicidal properties, active compositions in the form of mixtures of such compounds with solid and liquid dispersible carrier vehicles, and methods for producing such compounds and for using such compounds in a new way especially for combating pests, e.g., arthropods and nematodes, with other and further objects becoming apparent from a study of the within specification and accompanying examples.

It is known from U.S. Pat. No. 2,754,243, and German Published Specification DOS No. 2,360,877 and DAS 1,140,580 that certain pyrimidin(6)ylthiono-(thiol)-phosphoric(phosphonic) acid esters, for example O,O-diethyl-O- [2-iso-propyl-4-methylpyrimidin(6)yl]- (Compound A) and O-ethyl-S-n-propyl-O-[2-isopropyl-4-methyl-pyrimidin(6)yl]-thiol-thionophosphoric acid esters (compound B) and O-ethyl-O-[2,4-dimethyl-pyrimidin(6)yl]-thionoethanephosphonic acid ester (Compound C), possess insecticidal and acaricidal properties.

The present invention now provides, as new compounds, the pyrimidin(5)yl(thiono)(thiol)-phosphoric(-phosphonic) acid esters and ester-amides of the general formula

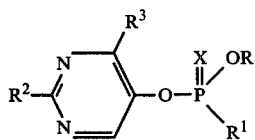
(I)

in which
R is alkyl,
R¹ is alkyl, alkoxy, alkylthio, monoalkylamino or phenyl,
R² is hydrogen, alkyl or phenyl,
R³ is hydrogen or alkyl, and
X is oxygen or sulphur.

Preferably, R represents straight-chain or branched alkyl with 1 to 6 (especially 1 to 4) carbon atoms, R¹ represents straight-chain or branched alkyl or alkoxy, alkylthio or monoalkylamino, each with 1 to 6 (especially 1 to 4) carbon atoms, or phenyl, R² represents hydrogen, phenyl or straight-chain or branched alkyl with 1 to 7 (especially 1 to 5) carbon atoms, R³ represents hydrogen or straight-chain or branched alkyl with 1 to 3 carbon atoms (especially methyl or ethyl) and X represents sulphur. In a preferred sub-group R is ethyl and R¹ is S-n-propyl.

Surprisingly, the pyrimidin(5)yl(thiono)(thiol)phosphoric(phosphonic) acid esters and ester-amides according to the invention exhibit a better insecticidal, acaricidal and nematicidal action than the known pyrimidin(6)yl-thiono(thiol)-phosphoric(phosphonic) acid esters of analogous structure and of the same type of action. The compounds of the present invention thus represent a genuine enrichment of the art.

The invention also provides a process for the preparation of a pyrimidin(5)yl(thiono)(thiol)-phosphoric(-phosphonic) acid ester or ester-amide of the formula (I), in which a (thiono)(thiol)-phosphoric(phosphonic) acid ester halide or ester-amide halide of the general formula

(II), in which
R, R¹ and X have the above-mentioned meanings and Hal represents halogen, preferably chlorine, is reacted, if appropriate in the presence of a solvent or diluent, with a 5-hydroxy-pyrimidine of the general formula

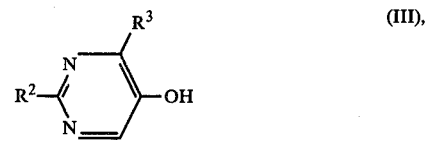
(III), in which
R² and R³ have the above-mentioned meanings, the latter being employed as such in the presence of an acid acceptor or in the form of an alkali metal salt, alkaline earth metal salt or ammonium salt.

If, for example, O-ethyl-S-n-propyl-thionothiolphosphoric acid diester chloride and 4-methyl-5-hydroxypyrimidine are used as starting materials, the course of the reaction can be represented by the following equation:

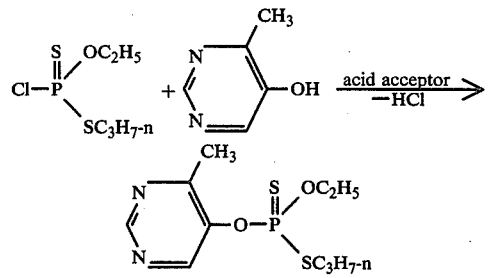

The (thiono)(thiol)phosphoric(phosphonic) acid ester halides and ester-amides halides (II) to be used as starting materials are known and can readily be prepared, even on an industrial scale, in accordance with processes known from the literature. The following may be mentioned as individual examples thereof: O,O-dimethyl-, O,O-diethyl-, O,O-di-n-propyl-, O,O-di-iso-propyl-, O,O-di-n-butyl-, O,O-di-iso-butyl-, O,O-di-sec.-butyl-, O-methyl-O-ethyl-, O-methyl-O-n-propyl-, O-methyl-O-iso-propyl-, O-methyl-O-n-butyl-, O-methyl-O-iso-butyl-, O-methyl-O-sec.-butyl-, O-ethyl-O-n-propyl-, O-ethyl-O-iso-propyl-, O-ethyl-O-n-butyl-, O-ethyl-O-sec.-butyl-, O-ethyl-O-iso-butyl-, O-n-propyl-O-butyl- and O-iso-propyl-O-butyl-phosphoric acid diester chloride and the corresponding thiono analogues; O,S-dimethyl-, O,S-diethyl-, O,S-di-n-propyl-, O,S-di-iso-propyl-, O,S-di-n-butyl-, O,S-di-iso-butyl-, O-ethyl-S-n-propyl-, O-ethyl-S-iso-propyl-, O-ethyl-S-n-butyl-, O-ethyl-S-sec.-butyl-, O-n-propyl-S-ethyl-, O-n-propyl-S-iso-propyl-, O-n-butyl-S-n-propyl- and O-sec.-butyl-S-ethyl-thiolphosphoric acid diester chloride and the corresponding thiono analogues; O-methyl-, O-ethyl-, O-n-propyl-, O-iso-propyl-, O-n-butyl-, O-iso-butyl- and O-sec.-butyl-methane-, ethane-, n-propane-, iso-propane-, N-butane-, iso-butane-, sec.-butane- and phenylphosphonic acid ester chloride and the corresponding thiono analogues; and O-methyl-N-methyl-, O-methyl-N-ethyl-, O-methyl-N-n-propyl-, O-methyl-N-iso-propyl-, O-ethyl-N-methyl-, O-ethyl-N-ethyl-, O-ethyl-N-n-propyl-, O-ethyl-N-iso-propyl-, O-n-propyl-N-methyl-, O-n-propyl-N-ethyl-, O-n-propyl-N-n-propyl-, O-n-propyl-N-isopropyl-, O-iso-propyl-N-methyl-, O-iso-propyl-N-ethyl-, O-iso-propyl-N-n-propyl-, O-iso-propyl-N-iso-propyl-, O-n-butyl-N-methyl-, O-n-butyl-N-ethyl-, O-n-butyl-N-n-propyl-, O-n-butyl-N-iso-propyl-, O-iso-butyl-N-methyl-, O-iso-butyl-N-ethyl-, O-iso-butyl-N-n-propyl-, O-iso-butyl-N-iso-propyl-, O-sec.-butyl-N-methyl-, O-sec.-butyl-N-ethyl-, O-sec.-butyl-N-n-propyl- and O-sec.-butyl-N-iso-propyl- phosphoric acid monoester-amide chloride and the corresponding thiono analogues.

Some of the 5-hydroxy-pyrimidines (III) also to be used as starting materials are new but can be prepared in accordance with processes known from the literature.

The following may be mentioned as individual examples thereof: 5-hydroxy-pyrimidine, 2-phenyl-, 2-methyl-, 2-ethyl-, 2-n-propyl-, 2-iso-propyl-, 2-n-butyl-, 2-iso-butyl-, 2-sec.-butyl-, 2-tert.-butyl-, 2-n-pentyl-, 2-phenyl-4-methyl-, 2,4-dimethyl-, 2-ethyl-4-methyl-, 2-n-propyl-4-methyl-, 2-iso-propyl-4-methyl-, 2-n-butyl-4-methyl-, 2-iso-butyl-4-methyl-, 2-sec.-butyl-4-methyl-, 2-tert.-butyl-4-methyl-, 2-phenyl-4-ethyl-, 2-methyl-4-ethyl-, 2,4-diethyl-, 2-n-propyl-4-ethyl-, 2-iso-propyl-4-ethyl-, 2-n-butyl-4-ethyl-, 2-iso-butyl-4-ethyl-, 2-sec.-butyl-4-ethyl-, 2-tert.-butyl-4-ethyl- and 2-n-pentyl-4-ethyl-5-hydroxy-pyrimidine.

The process for the preparation of the compounds according to the invention is preferably carried out in the presence of a suitable solvent or diluent. Virtually all inert organic solvents can be used for this purpose, especially aliphatic and aromatic, optionally chlorinated, hydrocarbons, such as benzene, toluene, xylene, benzine, methylene chloride, chloroform, carbon tetrachloride and chlorobenzene; ethers, for example diethyl ether, dibutyl ether and dioxane; ketones, for example acetone, methyl ethyl ketone, methyl isopropyl ketone and methyl isobutyl ketone; and nitriles, such as acetonitrile and propionitrile.

All customary acid-binding agents can be used as acid acceptors. Alkali metal carbonates and alkali metal alcoholates, such as sodium carbonate and potassium carbonate, sodium methylate and ethylate and potassium methylate, ethylate and tert.-butylate, have proved particularly suitable, as have aliphatic, aromatic or heterocyclic amines, for example triethylamine, trimethylamine, dimethylaniline, dimethylbenzylamine and pyridine.

The reaction temperature can be varied within a fairly wide range. In general, the reaction is carried out at from 0° to 100° C, preferably at from 20° to 60° C.

In genera, the reaction is allowed to take place under normal pressure.

To carry out the process, the starting materials are preferably employed in equimolar amounts. An excess of one or the other reactant produces no significant advantages.

In general, the reactants are combined in one of the stated solvents and are stirred for one or more hours, in most cases at an elevated temperature, to complete the reaction. After cooling, an organic solvent, for example toluene, is added to the mixture and the organic phase is worked up in the usual manner by washing, drying, and distilling off the solvent.

The new compounds are obtained in the form of oils, which in most cases cannot be distilled without decomposition, but are freed from the last volatile constituents by so-called "slight distillation", that is to say by prolonged heating under reduced pressure to moderately elevated temperatures, and are purified in this way. They are characterized by the refractive index.

As already mentioned, the compounds according to the present invention are distinguished by an excellent insecticidal, acaricidal and nematicidal activity. They are therefore active against plant pests, pests harmful to health and pests of stored products and combine a low phytotoxicity with a good action against sucking and biting insects and against mites.

For this reason, the compounds according to the invention can be employed successfully as pesticides in plant protection and in the hygiene field and the field of protection of stored products.

The compounds according to the present invention can also be used in the field of veterinary medicine.

The active compounds are well tolerated by plants, have a favorable level of toxicity to warm-blooded animals, and can be used for combating arthropod pests, especially insects and arachnids, and nematode pests which are encountered in agriculture, in forestry, in the protection of stored products and of materials, and in the hygiene field. They are active against normally sensitive and resistant species and against all or some stages of developement. The abovementioned pests include:

from the class of the *Isopoda*, for example *Oniscus asellus, Armadillidium vulgare* and *Porcellio scaber;* from the class of the *Diplopoda*, for example *Blaniulus guttulatus;* from the class of the *Chilopoda*, for example *Geophilus carpophagus* and *Scutigera* spec.;

from the class of the *Symphyla*, for example *Scutigeralla immaculata;* from the order of the *Thysanura*, for example *Lepisma saccharina;* from the order of the *Collembola*, for example *Onychiurus armatus;* from the order of the *Orthoptera*, for example *Blatta orientalis, Periplaneta americana, Leuchophaea maderae, Blattella germanica, Acheta domesticus, Gryllotalpa* spp., *Locusta migratoria migratorioides, Melanoplus differentialis* and *Schistocerca gregaria;* from the order of the *Dermaptera*, for example *Forficula auricularia;* from the order of the *Isoptera*, for example *Reticulitermes* spp.;

from the order of the *Anoplura*, for example *Phylloxera vastatrix, Pemphigus* spp., *Pediculus humanus corporis, Haematopinus* spp. and *Linognathus* spp.;

from the order of the *Mallophaga*, for example *Trichodectes* spp. and *Damalinea* spp.;

from the order of the *Thysanoptera*, for example *Hercinothrips femoralis* and *Thrips tabaci;* from the order of the *Heteroptera*, for example *Eurygaster* spp., *Dysdercus intermedius, Piesma quadrata, Cimex lectularius, Rhodnius prolixus* and *Triatoma* spp.;

from the order of the *Homoptera*, for example *Aleurodes brassicae, Bemisia tabaci, Trialeurodes vaporariorum, Aphis gossypii, Brevicoryne brassicae, Cryptomyzus*

*ribis, Doralis fabae, Doralis pomi, Eriosoma lanigerum, Hyalopterus arundinis, Macrosiphum avenae, Myzus* spp., *Phorodon humuli, Rhopalosiphum padi, Empoasca* spp., *Euscelis bilobatus, Nephotettix cincticeps, Lecanium corni, Saissetia oleae, Ladodelphax striatellus, Nilaparvata lugens, Aonidiella aurantii, Aspidiotus hederae, Pseudococcus* spp. and *Psylla* spp.;

from the order of the *Lepidoptera*, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Laphygma exigua, Mamestra brassicea, Panolis flammea, Prodenia litura, Spodoptera* spp., *Trichoplusia ni, Carpocapsa pomonella, Pieris* spp., *Chilo* spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the *Coleoptera*, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Ephilachna varivestis, Atomaria* spp., *Oryzaephilus surinamensis, Anthonomus* spp., *Sitophilus* spp., *Othiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis* and *Costelytra zealandica;* from the order of the *Hymenoptera*, for example *Diprion* spp., *Hoplocampa* spp., *Lasius* spp., *Monomorium pharanolis* and *Vespa* spp.;

from the order of the *Diptera*, for example *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae* and *Tipula paludosa;* from the order of the *Siphonaptera*, for example *Xenopsylla cheopis* and *Certatophyllus* ssp.;

from the class of the *Arachnida*, for example *Scorpio maurus* and *Latrodectus mactans;* from the order of the *Acarina*, for example *Acarus siro, Argas* spp., *Ornithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp. and *Tetranychus* spp.;

The plant-parasitic nematodes include *Pratylenchus* spp., *Radopholus similis, Ditylenchus dipsaci, Tylenchulus semipenetrans, Heterodera* spp., *Meloidogyne* spp., *Aphelenchoides* spp., *Longidorus* spp., *Xiphineam* spp., and *Trichodorus* spp..

When used against hygiene pests and pests of stored products, the active compounds are distinguished by an excellent residual activity on wood and clay as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, wettable powders, suspensions, powders, dusting agents, foams, pastes, soluble powers, granules, aerosols, suspension-emulsion concentrates, seed-treatment powders, natural and synthetic materials impregnated with active compound, very fine capsules in polymeric substances and in coating compositions, for use on seed, and formulations used with burning equipment, such as fumigating cartridges, fumigating cans, fumigating coils and the like, as well as ULV cold mist and warm mist formulations.

These are prepared in known manner, for instance by extending the active compounds with conventional pesticide dispersible liquid diluent carries and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as halogenated hydrocarbons, e.g, dichlorodifluoromethane and trichlorofluoromethane, as well as butane, propane, nitrogen and carbon dioxide; inert dispersible liquid diluent carriers, including inert organic solvents, such as aromatic hyrocarbons (e.g. benzene, toluene, xylene, alkyl naphthalenes, etc.). halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as solid carriers, ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules; crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; whereas the following may be chiefly considered for use as conventional carrier vehicle assistants, e.g., surface-active agents, for this purpose: emulsifying agents, such as non-ionic and/or amionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin-sulfite waste liquors, methyl cellulose, etc.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Pressian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Such active compounds may be employed alone or in the form of mixtures with one another and/or with such solid and/or liquid dispersible carrier vehicles and/or with other known compatible active agents, especially plant protection agents, such as other arthropodicides and nematicides, or fungicides, bactericides, rodenticides, herbicides, fertilizers, growth-regulating agents; etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0000001–100, preferably 0.01–10%, by weight of the mixture. Thus, the present invention contemplates overall compositions which comprise mixtures of a conventional dispersible carrier such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compostions with said liquid carrier vehicles containing from about 20 to about 95% by weight of the active compound or even the 100% active substance alone, e.g. about 20–100% by weight of the active compound.

When used against nematodes, the preparations are generally applied to an area of agriculture in amounts of 1 to 100 kg of active compound per hectare, and are then incorporated into the soil.

Furthermore, the present invention contemplates methods of selectively killing, combating or controlling pests, e.g. arthropods and neamtodes which comprise applying to at least one of correspondingly (a) such arthropods, (b) such nematodes, and (c) the corresponding habitat thereof, i.e. the locus to be protected, e.g. to a growing crop, to an area where a crop is to be grown or to a domestic animal, a correspondingly combative or toxic amount, i.e. an arthropodicidally or nematicidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dry dressing, moist dressing, wet dressing, slurry dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The preparation of the new compounds of the present invention is illustrated, without limitation, by the following examples:

EXAMPLE 1

The 5-hydroxy-pyrimidines (III) to be employed as starting materials could be prepared, for example, as follows:

(III a)

A solution of 49.5 g (0.45 mol) of 5-methoxypyrimidine [for its preparation see H. Bredereck et al., Chem. Ber. 91, (1958) page 2,848] and 38 g (0.68 mol) of potassium hydroxide in a mixture of 80 ml of water and 170 ml of methanol was heated for 3 hours to 190° C in an autoclave. The methanol was then distilled off, 50 ml of ice-water were added to the residue and the solution was brought to a pH value of 4.5 by adding concentrated hydrochloric acid while cooling. After 30 minutes, the product which had crystallized out was filtered off and 30 g (70% of theory) of 5-hydroxypyrimidine were thus obtained as a pale brown-colored crystal powder of melting point 208° C.

The following compounds of the formula

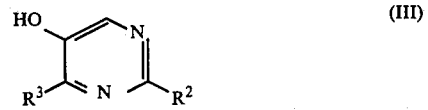
(III)

could be prepared analogously:

Table I

| Compound III | $R^2$ | $R^3$ | Yield (% of theory) | Melting point (° C) |
|---|---|---|---|---|
| b) | $C_3H_7$-iso | H | 72 | 185 |
| c) | $CH_3$ | H | 64 | 173 |
| d) | ⌬ | H | 94 | 144 |
| e) | $C_2H_5$ | H | | |
| f) | $C_3H_7$-n | H | | |
| g) | $C_4H_9$-n | H | | |

EXAMPLE 2

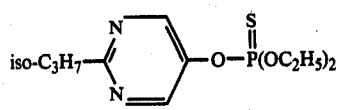 (1)

A mixture of 300 ml of acetonitrile, 13.8 g (0.1 mol) of 2-isopropyl-5-hydroxy-pyrimidine, 20.7 g (0.15 mol) of potassium carbonate and 18.8 g (0.1 mol) of O,O-diethylthionophosphoric acid diester chloride was stirred for 2 hours at 45° C. The reaction mixture was then poured into 400 ml of toluene and washed twice with 300 ml of water at a time. The toluene solution was dried over sodium sulphate and evaporated in vacuo. The residue was subjected to slight distillation in a high vacuum. 17.4 g (62% of theory of O,O-diethyl-O-[2-isopropyl-pyrimidin(5)yl]-thionophosphoric acid ester were thus obtained in the form of a brown oil having a refractive index $n_D^{21}$ of 1.4970.

The following compounds of the formula

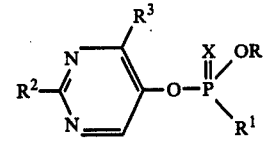 (I)

could be prepared analogously:

| Compound No. | R | $R^1$ | $R^2$ | $R^3$ | X | Yield (% of theory) | Refractive index: |
|---|---|---|---|---|---|---|---|
| 2 | $C_3H_7$-iso | $CH_3$ | $C_3H_7$-iso | H | S | 74 | $n_D^{21}$:1,5102 |
| 3 | $CH_3$ | $OCH_3$ | $C_3H_7$-iso | H | S | 66 | $n_D^{24}$:1,5080 |
| 4 | $C_2H_5$ | $SC_3H_7$-n | $C_3H_7$-iso | H | S | 69 | $n_D^{26}$:1,5284 |
| 5 | $C_2H_5$ | $C_6H_5$- | $C_3H_7$-iso | H | S | 74 | $n_D^{26}$:1,5570 |
| 6 | $C_2H_5$ | $OC_2H_5$ | $C_3H_7$-iso | H | O | 82 | $n_D^{32}$:1,4630 |
| 7 | $C_2H_5$ | $NH-C_3H_7$-iso | $C_3H_7$-iso | H | S | 57 | $n_D^{32}$:1,5057 |
| 8 | $C_3H_7$-n | $OC_2H_5$ | $C_3H_7$-iso | H | S | 73 | $n_D^{32}$:1,4929 |
| 9 | $C_2H_5$ | $OC_2H_5$ | $CH_3$ | H | S | 92 | $n_D^{32}$:1,4992 |
| 10 | $C_2H_5$ | $C_2H_5$ | $CH_3$ | H | S | 80 | $n_D^{32}$:1,5169 |
| 11 | $C_2H_5$ | $OC_2H_5$ | $C_6H_5$- | H | S | 80 | $n_D^{32}$:1,5643 |
| 12 | $C_2H_5$ | $C_2H_5$ | $C_6H_5$- | H | S | 80 | $n_D^{32}$:1,5827 |
| 13 | $C_2H_5$ | $OC_2H_5$ | H | H | S | 72 | $n_D^{32}$:1,5028 |
| 14 | $C_2H_5$ | $OC_2H_5$ | $C_2H_5$ | H | S | | |
| 15 | $C_2H_5$ | $OC_2H_5$ | $C_3H_7$-n | H | S | | |
| 16 | $C_2H_5$ | $OC_2H_5$ | $C_4H_9$-n | H | S | | |
| 17 | $C_2H_5$ | $OC_2H_5$ | $C_3H_7$-iso | $CH_3$ | S | | |
| 18 | $C_2H_5$ | $NH-C_3H_7$iso | $CH_3$ | H | S | 70 | $n_D^{23}$:1,5171 |
| 19 | $C_2H_5$ | $S-C_3H_7$n | H | H | O | 61 | $n_D^{23}$:1,5103 |
| 20 | $C_2H_5$ | $NH-C_3H_7$-iso | $C_3H_7$-iso | H | O | 56 | $n_D^{22}$:1,4831 |
| 21 | $C_2H_5$ | $NH-C_3H_7$-iso | $CH_3$ | H | O | | |
| 22 | $CH_3$ | $NH-C_3H_7$-iso | $C_3H_7$-iso | H | S | | |
| 23 | $CH_3$ | $NH-C_3H_7$-iso | $CH_3$ | H | S | | |
| 24 | $C_2H_5$ | $NH-C_3H_7$-iso | $C_2H_5$ | H | S | | |

The insecticidal, acaricidal and nematicidal activity of the compounds of this invention is illustrated by the following examples in which the compounds according to the present invention are each identified by the number (given in brackets) from the preparative examples hereinabove.

The known comparison compounds are identified as follows:

(A) = 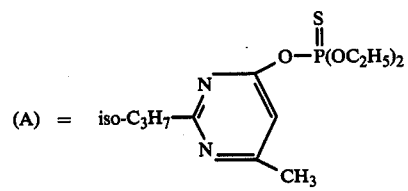

-continued (B) = iso-C₃H₇ — [pyrimidine ring with CH₃, O-P(=S)(OC₂H₅)(SC₃H₇-n)]

(C) = CH₃ — [pyrimidine ring with CH₃, O-P(=S)(C₂H₅)(OC₂H₅)]

EXAMPLE 3

Phaedon larvae test
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were sprayed with the preparation of the active compund until dripping wet and were then infested with mustard beetle larvae (*Phaedon cochleariae*).

After the specified periods of time, the degree of destruction was determined in % : 100% meant that all of the beetle larvae had been killed whereas 0% meant that none of the beetle larvae had been killed.

The active compounds, the concentration of the active compounds, the evaluation times and the results can be seen from the following table:

Table 3

| Active compound | (*Phaedon* larvae test) Active compound concentration in % | Degree of destruction in % after 3 days |
|---|---|---|
| (A) | 0.01 | 100 |
|  | 0.001 | 0 |
| (B) | 0.01 | 100 |
|  | 0.001 | 0 |
| (13) | 0.01 | 100 |
|  | 0.001 | 100 |
| (9) | 0.01 | 100 |
|  | 0.001 | 100 |
| (10) | 0.01 | 100 |
|  | 0.001 | 100 |
| (3) | 0.01 | 100 |
|  | 0.001 | 100 |
| (6) | 0.01 | 100 |
|  | 0.001 | 100 |
| (1) | 0.01 | 100 |
|  | 0.001 | 100 |
| (8) | 0.01 | 100 |
|  | 0.001 | 100 |
| (2) | 0.01 | 100 |
|  | 0.001 | 100 |
| (5) | 0.01 | 100 |
|  | 0.001 | 100 |
| (11) | 0.01 | 100 |
|  | 0.001 | 100 |
| (12) | 0.01 | 100 |
|  | 0.001 | 100 |

EXAMPLE 4

Tetranychus test (resistant)
Solvent: 3 parts by weight of acetone
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Bean plants (*Phaseolus vulgaris*) which were heavily infested with the two-spotted spider mite (*Tetranychus urticae*) in all stages of development were sprayed with the preparation of the active compound until dripping wet.

After the specified periods of time, the degree of destruction was determined as a percentage: 100% meant that all of the spider mites were killed whereas 0% meant that none of the spider mites were killed.

The active compounds, the concentrations of the active compounds, the evaluation times and the results can be seen from the following table:

Table 4

| Active compound | (*Tetranychus* test) Active compound concentration in % | Degree of destruction in % after 2 days |
|---|---|---|
| (A) | 0.1 | 95 |
|  | 0.01 | 0 |
| (B) | 0.1 | 98 |
|  | 0.01 | 0 |
| (13) | 0.1 | 100 |
|  | 0.01 | 90 |
| (9) | 0.1 | 100 |
|  | 0.01 | 95 |
| (10) | 0.1 | 100 |
|  | 0.01 | 70 |
| (3) | 0.1 | 100 |
|  | 0.01 | 90 |
| (1) | 0.1 | 98 |
|  | 0.01 | 80 |
| (2) | 0.1 | 100 |
|  | 0.01 | 90 |
| (4) | 0.1 | 100 |
|  | 0.01 | 90 |

EXAMPLE 5

Test insects: *Sitophilus granarius*
Solvent: Acetone

The active compound was taken up in the solvent at a rate of 2 g per liter. The solution so obtained was diluted with further solvent to the desired concentrations.

2.5 ml of the solution of the active compounds were pipetted into a Petri dish. On the bottom of the Petri dish there was a filter paper with a diameter of about 9.5 cm. The Pertri dish remained uncovered until the solvent had completely evaporated. The amount of active compound per square meter of filter paper varied with the concentration of the solution of active compound. About 25 test insects were then placed in the Petri dish and it was covered with a glass lid.

The condition of the test insects was observed 3 days after the commencement of the experiments. The destruction, in %, was determined. 100% denoted that all of the test insects had been killed; 0% denoted that none of the test insects had been killed.

The active compounds, the concentrations of the active compounds, and the results can be seen from the following table:

Table 5

| Active compound | (*Sitophilus granarius*) Active compound concentration of the solution in % | Degree of destruction in % |
|---|---|---|
| (B) | 0.002 | 0 |
| (C) | 0.002 | 0 |
| (3) | 0.002 | 100 |
| (1) | 0.002 | 100 |
| (2) | 0.002 | 100 |

EXAMPLE 6

Test insects *Blatta orientalis*
Solvent: Acetone

The active compound was taken up in the solvent at a rate of 2 g per liter. The solution so obtained was diluted with further solvent to the desired concentrations.

2.5 ml of the solution of the active compound were pipetted into a Petri dish. On the bottom of the Petri dish there was a filter paper with a diameter of about 9.5 cm. The Petri dish remained uncovered until the solvent had completely evaporated. The amount of active compound per square meter of filter paper varied with the concentration of the solution of active compound. About 25 test insects were then placed in the Petri dish and it was covered with a glass lid.

The condition of the test insects was observed 3 days after the commencement of the experiments. The destruction, in %, was determined. 100% denoted that all of the test insects had been killed; 0% denoted that none of the test insects had been killed.

The active compounds, the concentrations of the active compounds, and the results can be seen from the following table:

Table 6

| Active compound | (*Blatta orientalis*) Active compound concentration of the solution in % | Degree of destruction in % |
|---|---|---|
| (B) | 0.02 | 0 |
| (3) | 0.02 | 100 |
| (1) | 0.002 | 100 |
| (2) | 0.02 | 100 |

EXAMPLE E

Critical concentration test/nematodes

EXAMPLE 7

Test nematode: *Meloidogyne incognita*
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil which was heavily infested with the test neamtodes. The concentration of the active compound in the preparation was of practically no importance; only the amount of active compound per unit volume of soil, which is given hereinafter in ppm (=mg/l), was decisive. The treated soil was filled into pots, lettuce was sown in and the pots were kept at a greenhouse temperature of 27° C.

After 4 weeks, the lettuce roots were examined for infestation with nematodes (root galls), and the degree of effectiveness of the active compound was determined as a percentage. The degree of effectiveness was 100% when infestation was completely avoided; it was 0% when the infestation was exactly the same as in the case of the control plants in untreated soil which had been infested in the same manner.

The active compound, the amounts applied and the results can be seen from the following table:

Table 7

| Active compound | Nematicides (*Meloidogyne incognita*) Degree of destruction in % at an active compound concentration of 10 ppm |
|---|---|
| (B) | 0 |
| (1) | 100 |
| (2) | 100 |
| (7) | 100 |

EXAMPLE 8

Test insect: *Tenebrio molitor* larvae in the soil
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The amount of active compound was intimately mixed with the soil. The concentration of the active compound in the preparation was practically immaterial, the only decisive factor being the amount by weight of active compound per unit volume of soil, which is quoted hereinafter in ppm (= mg/l). The treated soil was filled into pots and the pots were left to stand at room temperature.

After 24 hours the test insects were introduced into the treated soil and after a further 2 to 7 days the degree of effectiveness of the active compound was determined in % by counting the dead and the live test insects. The degree of effectiveness was 100% if all of the test insects had been killed and was 0% if exactly as many test insects were still alive as in the case of the untreated control.

The active compounds, the amounts used and the results can be seen from the table which follows:

Table 8

| Active compound | Soil insects (*Tenebrio molitor* larvae in the soil) Degree of destruction in % at an active compound concentration of 2.5 ppm |
|---|---|
| (A) | 0 |
| (B) | 0 |
| (1) | 100 |
| (2) | 100 |
| (8) | 100 |

EXAMPLE 9

Root-sytemic action
Test insect: *Phaedon cochleariae* larvae

Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was of practically no importance; only the amount of active compound per unit volume of soil, which is given hereinafter in ppm (= mg/1), was decisive. The treated soil was filled into pots and these were planted with cabbage (*Brassica oleracea*). The active compound could in this way be taken up from the soil by the plant roots and be transported into the leaves.

To demonstrate the root-systemic effect, only the leave were infested with the above-mentioned test insects after 7 days. After a further 2 days, the results were evaluated by counting or estimating the dead insects. The root-systemic acition of the acitve compound was deduced from the destruction data. It was 100% when all of the test insects had been killed and 0% when just as many test insects were still alive as in the case of the untreated control.

The active compounds, the amounts used and the results can be seen from the following table:

Table 9

| Active compound | Root-systemic action (*Phaedon cochleariae* larvae) Degree of destruction in % at an active compound concentration of 20 ppm |
|---|---|
| (A) | 0 |
| (B) | 0 |
| (1) | 100 |
| (2) | 100 |
| (10) | 100 |
| (13) | 100 |
| (7) | 100 |

EXAMPLE 10

Root-systemic action
Test animal: *Myzus persicae*
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was of practically no importance; only the amount of active compound per unit volume of soil, which is given hereinafter in ppm (= mg/1), was decisive. The treated soil was filled into pots and these were planted with cabbage (*Brassica oleracea*). The active compound could in this way be taken up from the soil by the plant roots and be transported into the leaves.

To demonstrate the root-systemic effect, only the leaves were infested with the above-mentioned test insects after 7 days. After a further 2 days, the results were evaluated by counting or estimating the dead insects. The root-systemic action of the active compound was deduced from the destruction data. It was 100% when all of the test insects had been killed and 0% when just as many test insects were still alive as in the case of the untreated control.

The active compounds, the amounts used and the results can be seen from the following table:

Table 10

| Active compound | Root-systemic action (*Myzus persicae*) Degree of destruction in % at an active compound concentration of 2.5 ppm |
|---|---|
| (B) | 0 |
| (1) | 100 |
| (2) | 100 |
| (9) | 100 |
| (10) | 100 |
| (13) | 100 |
| (7) | 100 |

It will be appreciated that the instant specification and claims are set forth by way of illustration and not limitation, and that various modifications and changes may be made without departing from the spirit and scope of the present invention.

What is claimed is:

1. An O-alkyl:O:[pyrimidin(5)yl](thiono)(thiol)-phosphoric(phosphonic) acid ester or ester-amide of the formula

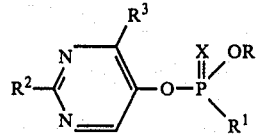

in which
R is alkyl with 1 to 6 carbon atoms,
$R^1$ is alkyl, alkoxy, alkylthio or monoalkylamino each with 1 to 6 carbon atoms,
$R^2$ is hydrogen, alkyl with 1 to 7 carbon atoms or phenyl,
$R^3$ is hydrogen or alkyl with 1 to 3 carbon atoms, and
X is oxygen or sulphur.

2. A compound according to claim 1, in which X is sulphur.

3. A compound according to claim 1, wherein the compound is O,O-diethyl-O-[2-iso-propyl-pyrimidin(5)yl]-thionophosphoric acid ester of the formula

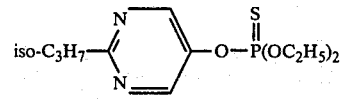

4. A compound according to claim 1, wherein the compound is O,O-dimethyl-O-[2-iso-propyl-pyrimidin(5)yl]-thionophosphoric acid ester of the formula

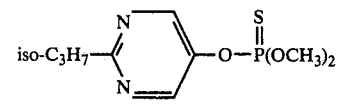

5. A compound according to claim 1, wherein the compound is O-ethyl-S-n-propyl-O-[2-iso-propyl-pyrimidin(5)yl]-thionothiolphosphoric acid ester of the formula

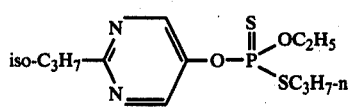

6. A compound according to claim 1, wherein the compound is O-ethyl-N-iso-propyl-O-[2-iso-propyl-pyrimidin(5)yl]-thionophosphoric acid ester amide of the formula

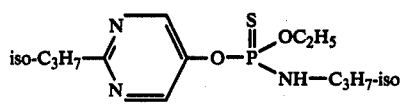

7. A compound according to claim 1, wherein the compound is O,O-diethyl-O-[2-phenyl-pyrimidin(5)yl]-thionophosphoric acid ester of the formula

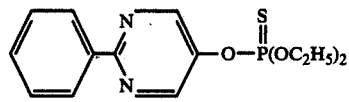

8. An arthropodicidal or nematicidal composition containing as active ingredient an arthropodicidally or nematicidally effective amount of a compound according to claim 1 in admixture with a diluent.

9. A method of combating arthropods or nematodes, which comprises applying to said arthropods or nematodes or to a habitat thereof, an arthropodicidally or nematicidally effective amount of a compound according to claim 1.

10. The method according to claim 9 in which said compound is
- O,O-diethyl-O-[2-iso-propyl-pyrimidin(5)yl]-thionophosphoric acid ester,
- O,O-dimethyl-O-[2-iso-propyl-pyrimidin(5)yl]-thionophosphoric acid ester,
- O-ethyl-S-n-propyl-O-[2-iso-propyl-pyrimidin(5)yl]-thionothiolphosphoric acid ester,
- O-ethyl-N-iso-propyl-O-[2-iso-propyl-pyrimidin(5)yl]-thionophosphoric acid ester amide, or
- O,O-diethyl-O-[2-phenyl-pyrimidin(5)yl]-thionophosphoric acid ester.

* * * * *